US008377683B2

(12) United States Patent
Lu et al.

(10) Patent No.: US 8,377,683 B2
(45) Date of Patent: Feb. 19, 2013

(54) ZINC OXIDE-BASED NANOSTRUCTURE MODIFIED QCM FOR DYNAMIC MONITORING OF CELL ADHESION AND PROLIFERATION

(75) Inventors: Yicheng Lu, East Brunswick, NJ (US); Pavel Ivanoff Reyes, Mountainside, NJ (US); Nada N. Boustany, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/555,721

(22) Filed: Jul. 23, 2012

(65) Prior Publication Data
US 2013/0017567 A1 Jan. 17, 2013

Related U.S. Application Data

(63) Continuation-in-part of application No. 13/193,057, filed on Jul. 28, 2011, now abandoned, which is a continuation of application No. 11/600,556, filed on Nov. 16, 2006, now Pat. No. 7,989,851, and a continuation-in-part of application No. 11/119,475, (Continued)

(51) Int. Cl.
*C12M 1/36* (2006.01)
*C12M 3/00* (2006.01)
*H01L 29/82* (2006.01)

(52) U.S. Cl. ............ 435/286.6; 435/288.7; 435/303.2; 257/252; 257/253; 257/414; 257/E23.165; 257/E23.081; 257/E29.093; 204/400; 204/403.13; 119/300; 119/311; 119/319; 55/385.2

(58) Field of Classification Search .............. 435/286.6, 435/288.7, 302.2; 257/252, 253, 414, E23.165, 257/E29.081, E29.093; 204/400, 403.13; 119/300, 311, 319; 55/385.2
See application file for complete search history.

(56) References Cited

U.S. PATENT DOCUMENTS

| | | | |
|---|---|---|---|
| 5,140,393 A | 8/1992 | Hijikihigawa et al. | |
| 5,440,189 A | 8/1995 | Nakahata et al. | |
| 6,304,020 B1 | 10/2001 | Lonsdale et al. | |
| 6,626,026 B2 | 9/2003 | Banda et al. | |
| 6,673,644 B2 | 1/2004 | Gole et al. | |
| 6,914,279 B2 | 7/2005 | Lu et al. | |
| 2002/0093398 A1 | 7/2002 | Ella et al. | |
| 2003/0201694 A1* | 10/2003 | Lu et al. | 310/313 A |
| 2004/0063195 A1* | 4/2004 | Tamaoki et al. | 435/286.6 |
| 2007/0048727 A1* | 3/2007 | Shuler et al. | 435/1.2 |
| 2007/0132043 A1 | 6/2007 | Bradley et al. | |

(Continued)

FOREIGN PATENT DOCUMENTS
| | | |
|---|---|---|
| WO | 99/35312 A1 | 7/1999 |
| WO | 99/54718 A1 | 10/1999 |

(Continued)

OTHER PUBLICATIONS

Emanetoglu et al. Mg.sub.xZn.sub.1-xO: A New Plezoelectric Material, IEEE Ultrasonics Symposium, pp. 253-256, 2001.

(Continued)

*Primary Examiner* — Dao H Nguyen
(74) *Attorney, Agent, or Firm* — Fox Rothschild LLP

(57) ABSTRACT

A dynamic and noninvasive method of monitoring the adhesion and proliferation of biological cells through multimode operation (acoustic and optical) using a ZnO nanostructure-modified quartz crystal microbalance ($ZnO_{nano}$-QCM) biosensor is disclosed.

11 Claims, 11 Drawing Sheets

Related U.S. Application Data filed on Apr. 29, 2005, now abandoned, which is a continuation of application No. 10/456,050, filed on Jun. 6, 2003, now Pat. No. 6,914,279.

(60) Provisional application No. 60/736,852, filed on Nov. 16, 2005, provisional application No. 60/385,884, filed on Jun. 6, 2002, provisional application No. 61/580,223, filed on Dec. 24, 2011.

(56) References Cited

U.S. PATENT DOCUMENTS

| | | | |
|---|---|---|---|
| 2007/0151508 A1* | 7/2007 | Lu et al. | 117/104 |
| 2012/0214225 A1* | 8/2012 | Oura et al. | 435/288.7 |

FOREIGN PATENT DOCUMENTS

| | | |
|---|---|---|
| WO | 02/07309 A2 | 1/2002 |
| WO | 02/17362 A2 | 2/2002 |

OTHER PUBLICATIONS

Kalantar-Zadeh et al. A Novel Love Mode SAW Sensor with ZnO layer Operating in Gas and Liquid Media, IEEE Ultrasonics Symposium, pp. 353-356, 2001.

Yuan et al. Current-Voltage Properties of Piezoelectric Thin Film ZnO in a Micromechanical Force sensor, IEEE Ultrasonics Symposium, pp. 593-596, 1998.

G. Marrazza, et al., "Disposable DNA Electrochemical Sensor for Hybridization Detection", Elsevier Science B. V., Biosensors & Bioelectronics 14 (1999), pp. 43-51.

Sara Tombelli, et al., "Coupling of a DNA Piezoelectric Biosensor and Polymerase Chain Reaction to Detect Apolipoprotein E Polymorphisms", Elsevier Science S.A., Biosensors & Bioelectronics 15 (2000), pp. 363-370.

T. Andrew Taton, et al., "Scanometric DNA Array Detection with Nanoparticle Probes", Science, vol. 289, pp. 1757-1760.

Linda A. Chrisey, et al., "Covalent Attachment of Synthetic DNA to Self-Assembled Monolayer Films", Nucleic Acids Research, vol. 24, No. 15, pp. 3031-3039.

Sangita Phadtare, et al., "Cold-Shock Response and Cold-Shock Proteins", Elsevier Science Ltd., Current Opinion in Microbiology 1999, vol. 2, pp. 175-180.

M.O. Nicoletto, et al., "BRCA-1 and BRCA-2 Mutations as Prognostic Factors in Clinical Practice and Genetic Counselling", Cancer Treatment Reviews, vol. 27, pp. 295-304.

Dan Tong, et al., "BRCAI Gene Mutations in Sporadic Ovarian Carcinomas: Detection by PCR and Reverse Allele-specific Oligonucleotide Hybridization", Clinical Chemistry, 45:7 (1999) pp. 976-981.

N. Barle, et al., Covalent Bound Sensing Layers on Surface Acoustic Wave (SAW), Elsevier Science B.V., Biosensors & Bioelectronics 16 (2001), pp. 979-987.

T. Wessa, et al., "New Immobilization Method for SAW-biosensors: Covalent Attachment of Antibodies via CNBr", Elsevier Science S.A., Biosensors & Bioelectronics 14 (1999) pp. 93-98.

Atsushi Miyawaki, et al., "Fluorescent Indicators for $Ca^{2+}$ Based on Green Fluorescent Proteins and Calmodulin", Nature, vol. 388, pp. 882-887.

Yi Cui, et al., "Nanowire Nanosensors for Highly Sensitive and Selective Detection of Biological and Chemical Species", Science, vol. 293, Aug. 2001, pp. 1289-1292.

Victor H. Perez-Luna, et al., "Fluorescence Biosensing Strategy Based on Energy Transfer Between Fluorescently Labled Receptors and a Metallic Surface", Elsevier B.V., Biosensors & Bioelectronics, 17 (2002), pp. 71-78.

H. Sheng, et al., "Nonalloyed Al Ohmic Contacts to $Mg_x Zn_{1-x}O$", Journal of Electronic Materials, vol. 31, pp. 811-814.

Kourosh Kalantar Zadeh et al., A Novel Love-mode Device based on a ZnO/ST-cut Quartz Crystal Structure for Sensing Applications, Elsevier Science B.V., Sensors and Actuators, A 100 (2002), pp. 135-143.

Sriram Muthukumar, et al., "Selective MOCVD Growth of ZnO Nanotips", IEEE Transactions on Nanotechnology, vol. 2, No. 1, Mar. 2003, pp. 50-54.

Jianming Ye, et al., "Piezoelectric Biosensor for Detection of *Salmonella typhimurium*", Journal of Food Science, vol. 62, pp. 1067-1086.

International Search Report from corresponding International Patent Application No. PCT/US03/17822, filed Jun. 6, 2003.

* cited by examiner

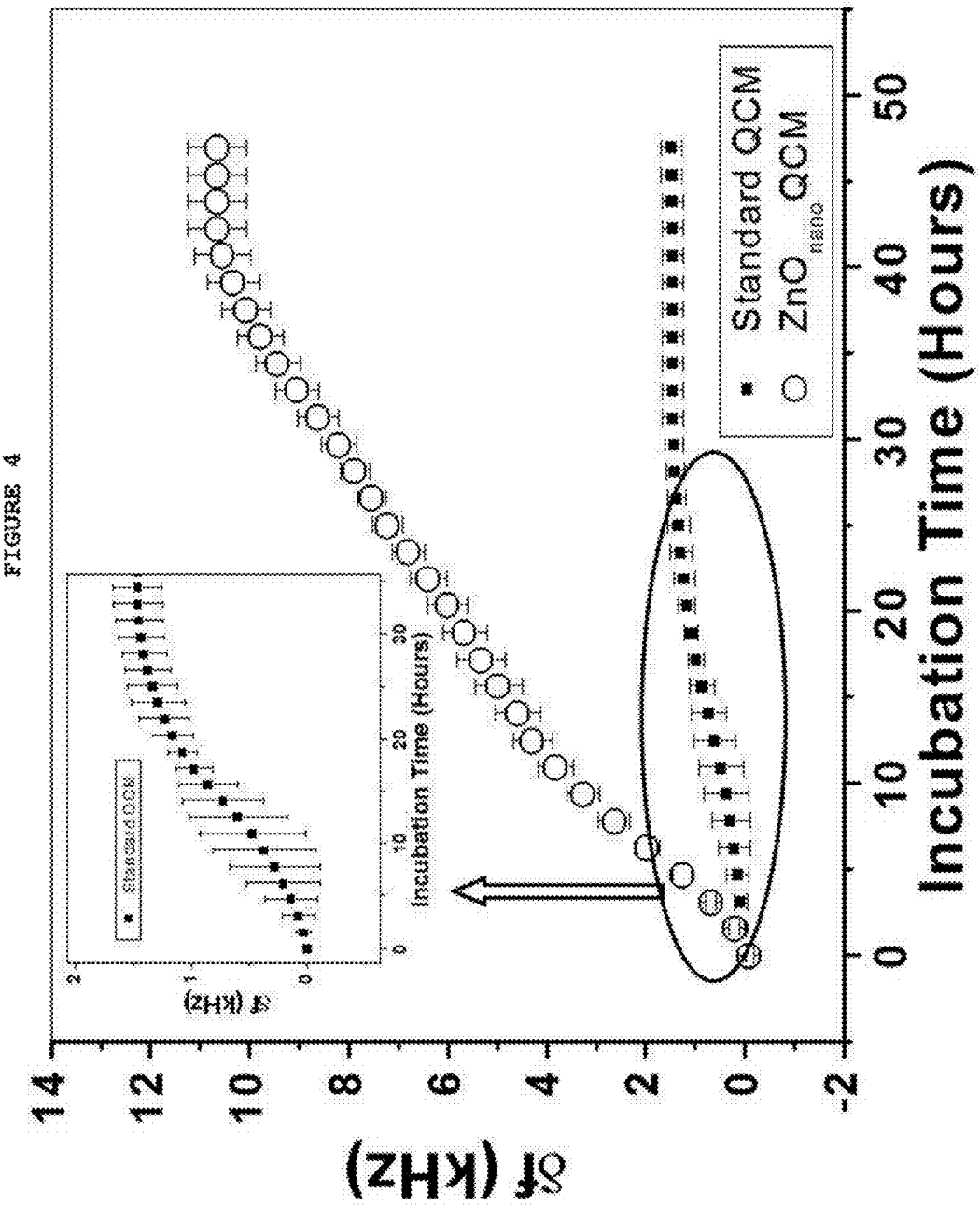

FIGURES 5 (a) – (b)
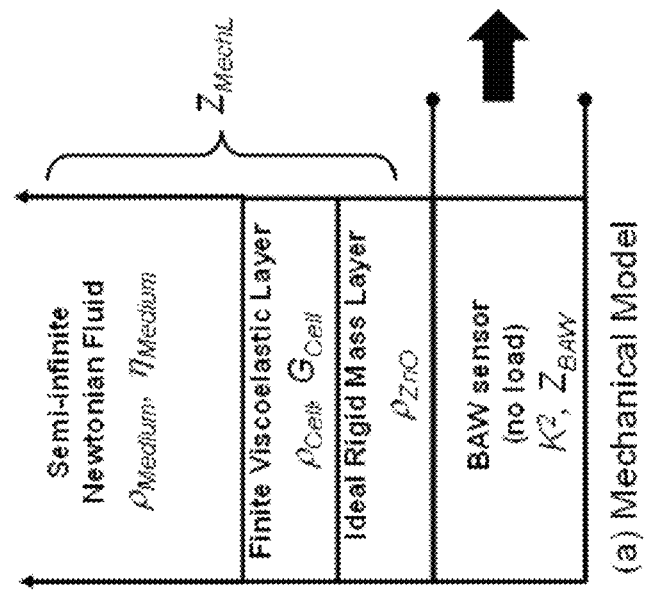
(b) Electrical Counterpart Model
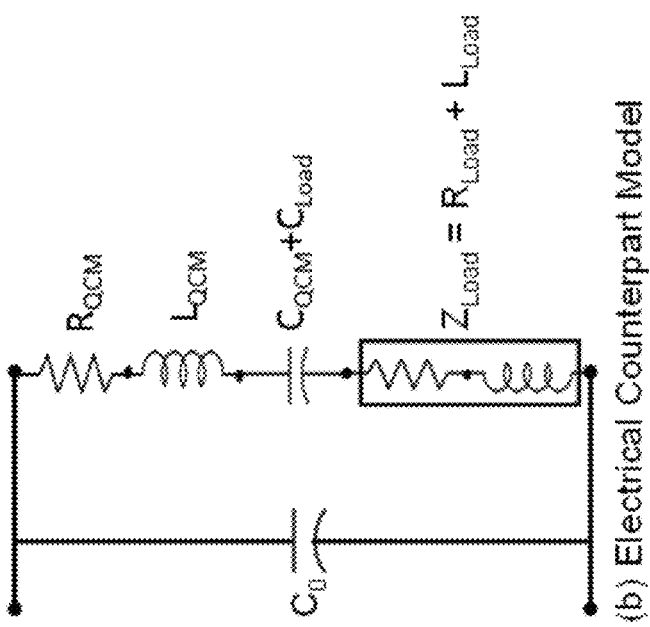
(a) Mechanical Model

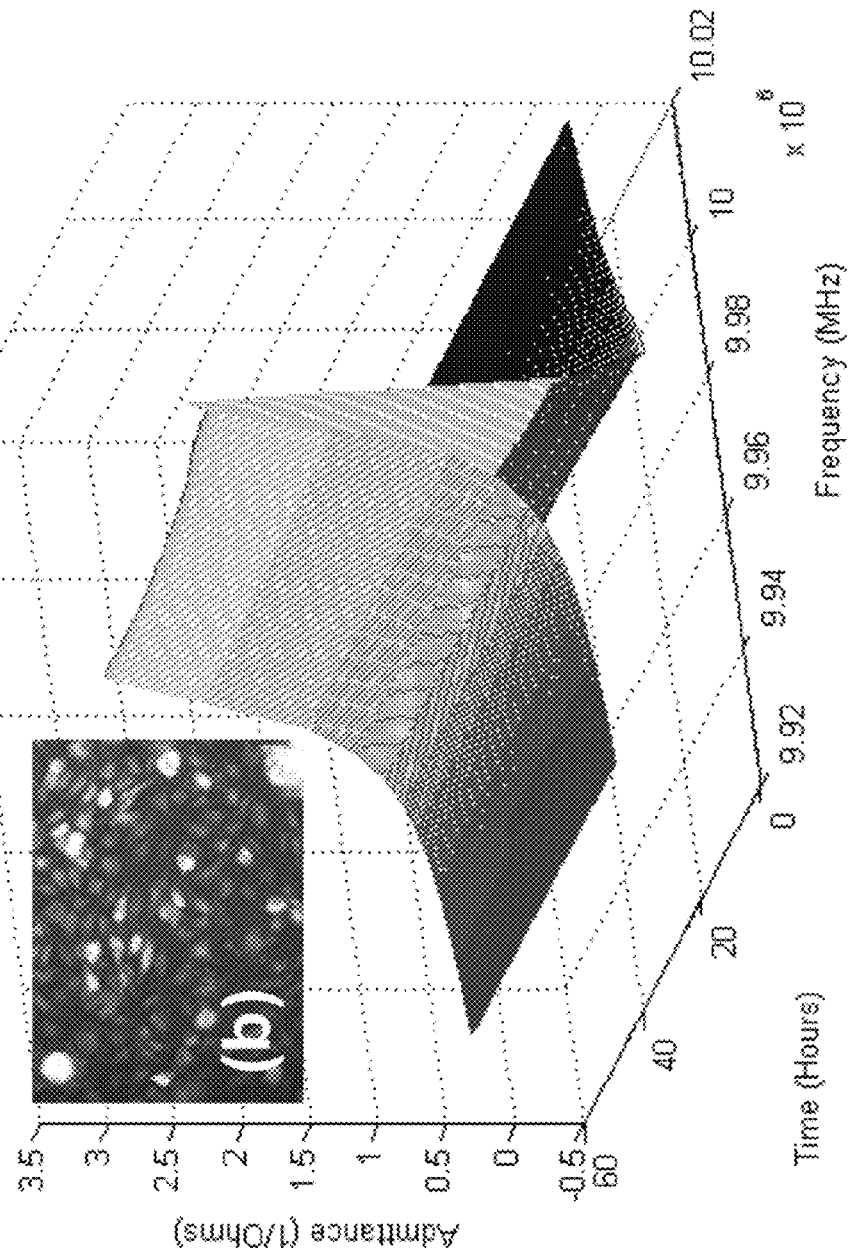
FIGURES 7 (a) – (b)

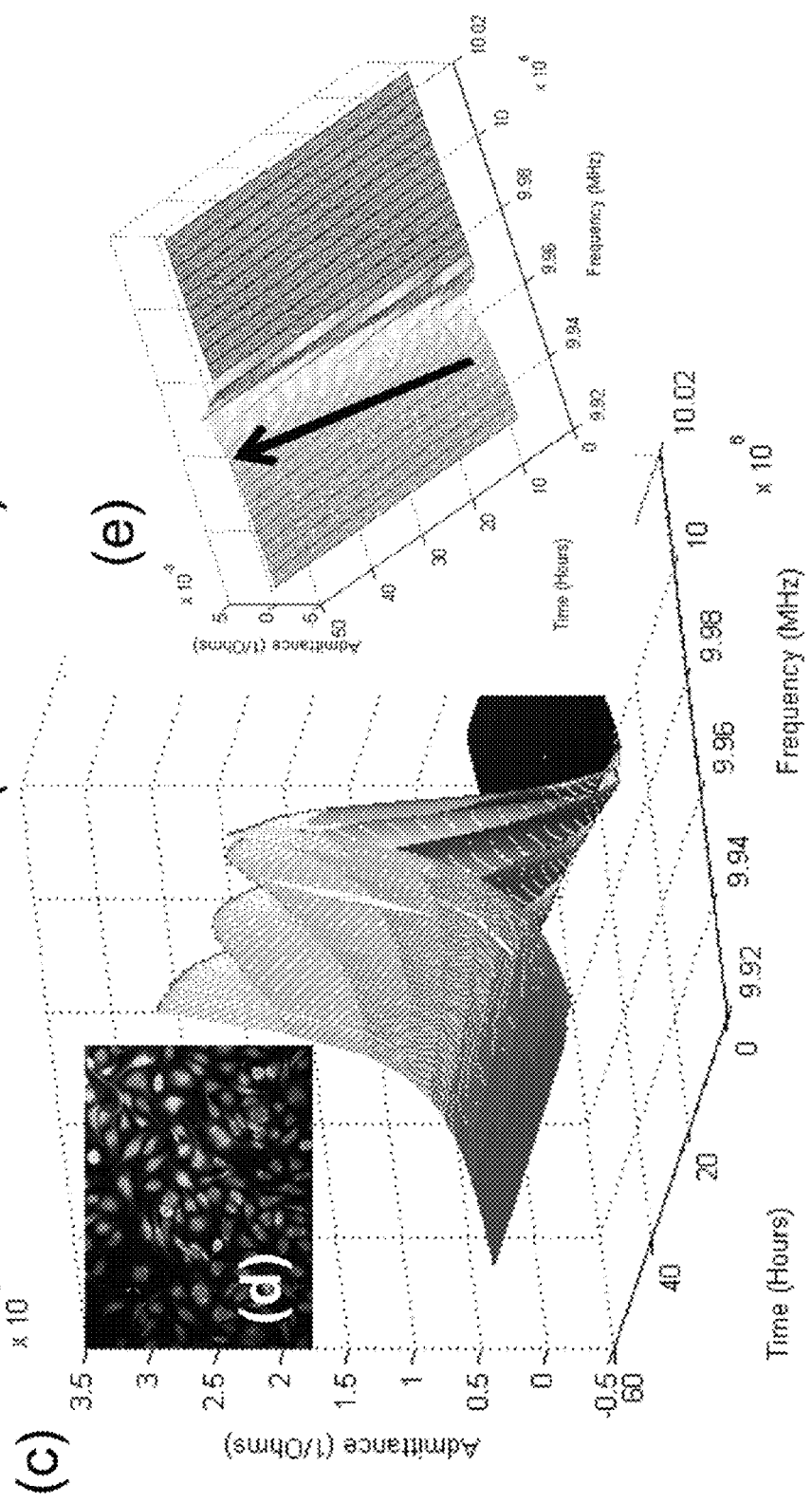
FIGURES 7 (c) – (e)

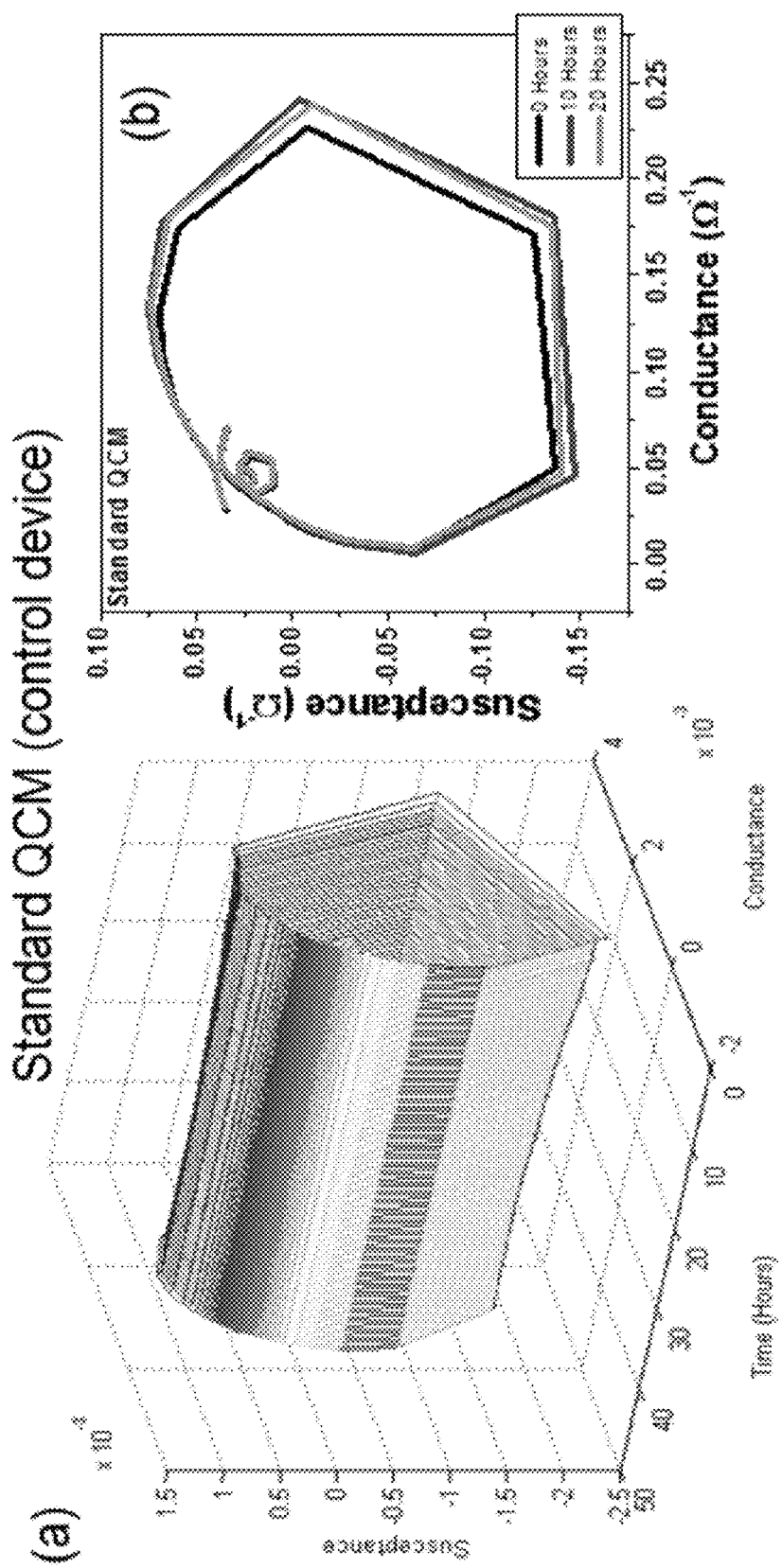
FIGURES 8 (a) – (b)

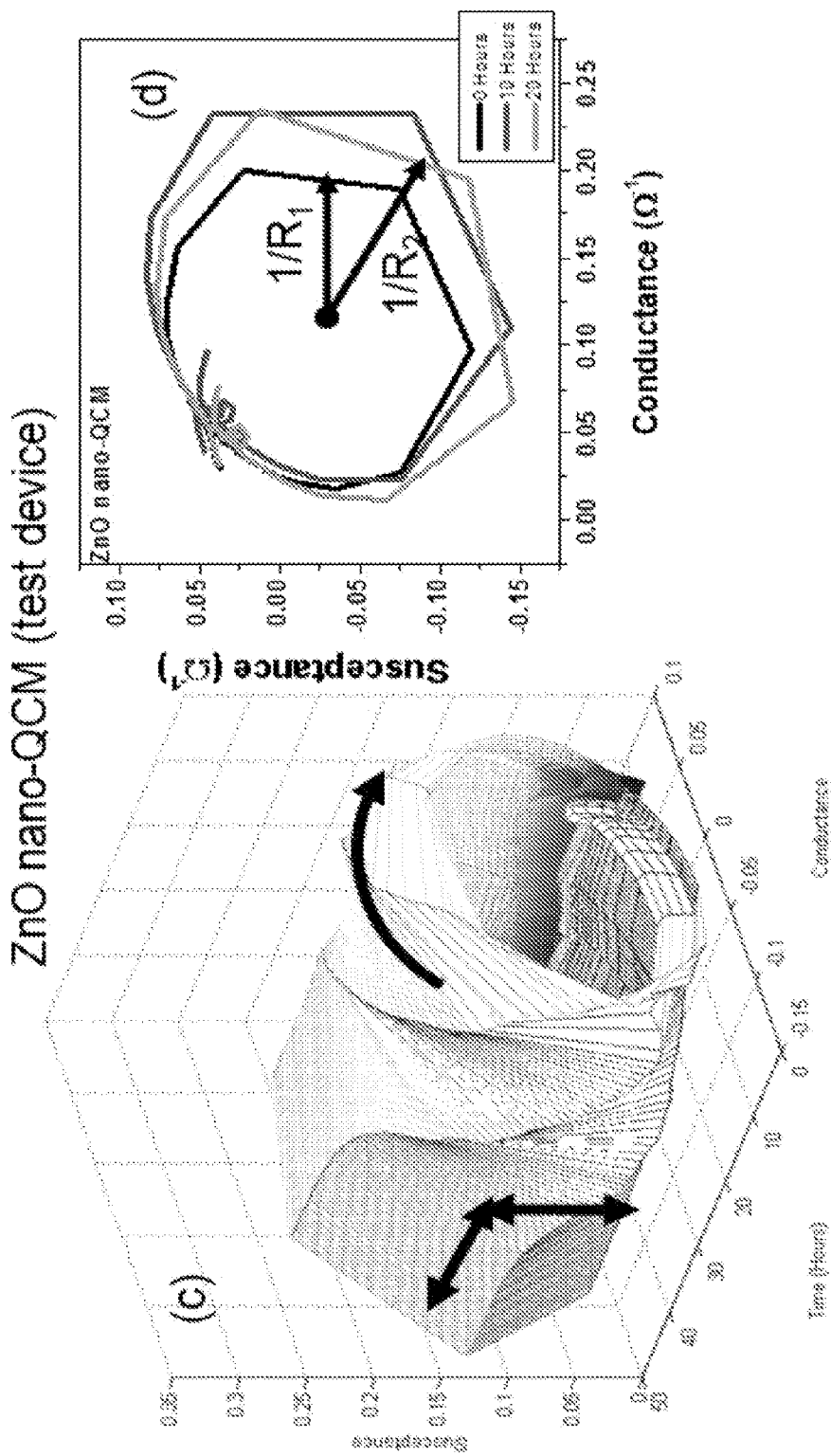
FIGURES 8 (c) – (d)

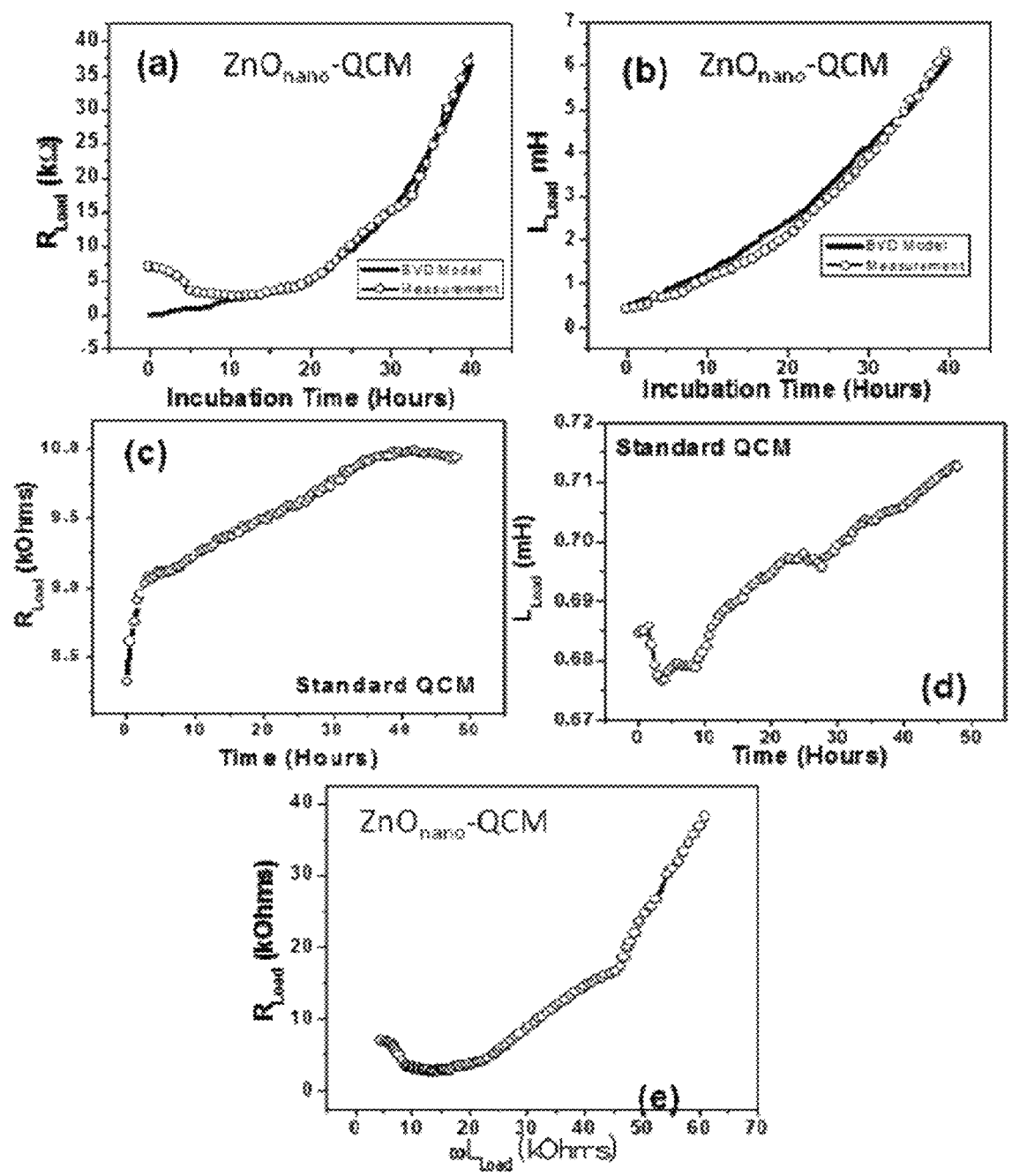
FIGURES 9 (a) – (e)

US 8,377,683 B2

ZINC OXIDE-BASED NANOSTRUCTURE MODIFIED QCM FOR DYNAMIC MONITORING OF CELL ADHESION AND PROLIFERATION

CROSS-REFERENCE TO RELATED APPLICATIONS

This application claims the benefit of U.S. Provisional Patent Application No. 61/580,223, filed on Dec. 24, 2011, and is a Continuation-in-Part of U.S. patent application Ser. No. 13/193,057, filed on Jul. 28, 2011, now abandoned which is a continuation of U.S. patent application Ser. No. 11/600,556, filed on Nov. 16, 2006, now U.S. Pat. No. 7,989,851, which claims the benefit of U.S. Provisional Patent Application No. 60/736,852, filed on Nov. 16, 2005. U.S. patent application Ser. No. 11/600,556 is also a Continuation-in-Part of U.S. patent application Ser. No. 11/119,475, filed on Apr. 29, 2005, now abandoned which is a continuation of U.S. patent application Ser. No. 10/456,050, filed on Jun. 6, 2003, now U.S. Pat. No. 6,914,279, and which claims the benefit of U.S. Provisional Patent Application No. 60/385,884, filed on Jun. 6, 2002. The contents of the foregoing applications are incorporated herein by reference in their entireties.

STATEMENT REGARDING FEDERALLY FUNDED RESEARCH

The research leading to the present invention was supported by Grant Nos. NSF ECS-008854, NSF CCR-0103096, and ECCS-1002178, awarded by the National Science Foundation, and Grant No. FA 9550-08-1-0452, awarded by the Air Force Office of Scientific Research. Accordingly, the U.S. Government has certain rights in this invention.

FIELD OF THE INVENTION

The present invention relates generally to sensors. More specifically, embodiments disclose a nanostructure-modified quartz crystal microbalance ($ZnO_{nano}$-QCM) having ZnO nanostructures with the suitable morphology directly grown on the top of the sensing electrode to enhance the sensor's sensitivity for dynamic and noninvasive monitoring of the adhesion and proliferation of cells.

BACKGROUND OF THE INVENTION

Non-invasive examination of live cell function in real time is essential in advancing understanding of the mechanistic and dynamic progression of biological processes. Understanding the biological processes involved in cell growth and death has a great impact on development of the cell-based drugs. It also complements the existing analytical tools that are aimed at gene and protein identification. The main issue with cellular measurements is that the physical properties do not directly report on a specific molecular target in a given cellular pathway. However, loss of homeostasis, alterations in molecular function and deregulation of molecular pathways inevitably manifest themselves as detectable physical changes in cellular properties.

There are numerous methods being used to monitor biological cell activity, where optical microscopy, hemacytometry, and flow cytometry are standard techniques. However, these standard methods often involve invasively killing the cells and tagging them with optically active biomolecules to obtain information about their growth, proliferation, and function. Recently, there has been an increased interest in developing non-invasive and label-free techniques in monitoring cell function. In vivo flow cytometry is one of the most recent developments in non-invasive cell monitoring, but is not label free. See Irene Georgakoudi, Nicolas Solban, John Novak, William L. Rice, Xunbin Wei, Tayyaba Hasan, and Charles P. Lin, "In Vivo Flow Cytometry: A New Method for Enumerating Circulating Cancer Cells," Cancer Research 64, 5044-5047, Aug. 1, 2004. It combines confocal microscopy and flow cytometry and is only limited to cells that are circulating in the bloodstream. This method is only used in animals, where cells are still invasively tagged with fluorescent markers to act as the label for the confocal microscope. Furthermore, due to expensive equipment and complicated operation involved, it is impossible to simultaneously monitor large numbers of the samples in real-time.

Non-optical biosensing devices have also been employed in cellular monitoring techniques. These devices are more compact and cost effective than the optical method. The most common method is the impedance spectrum analysis using the standard quartz crystal microbalance (QCM) and the QCM with dissipation (QCM-D), and the E-Plate impedance sensor. These techniques however are not very sensitive to viscoelastic transitions occurring in biological samples. Moreover, since their sensing area surfaces are not controllable, they also require surface-conditioning chemicals to facilitate bio-adhesion to the metallic sensing surface and involves only a limited number of these compatible chemicals. See C. Fredriksson, S. Kihlman, M. Rodahl, B. Kasemo, "The Piezoelectric Quartz Crystal Mass and Dissipation Sensor: A Means of Studying Cell Adhesion," Langmuir, 14 248-251, 1998; X. C. Zhou, L. Q. Huang, and S. F. Y. Li, "Microgravimetric DNA sensor based on quartz crystal microbalance: comparison of oligonucleotide immobilization methods and the application in genetic diagnosis," Biosensors & Bioelectronics, vol. 16, pp. 85, 2001, M. Muratsugu, F. Ohta, Y. Miya, T. Hosokawa, S. Kurosawa, N. Kamo, and H. Ikeda, "Quartz crystal microbalance for the detection of microgram quantities of human serum albumin: relationship between the frequency change and the mass of protein adsorbed," Analytical Chemistry, vol. 65, pp. 2933, 1993.

Accordingly, there is an immediate need for improved sensors and related sensing methods.

SUMMARY OF THE INVENTION

There is provided, in accordance with the present invention, a dynamic and noninvasive cell adhesion and cell proliferation monitoring system, that includes: a bulk acoustic wave (BAW) sensor deployed inside at least one cell-growth well deployed within a temperature controlled $CO_2$ incubator wherein the sensor device includes: a piezoelectric layer; a conductive film serving as a bottom electrode deposited and patterned beneath the piezoelectric layer; a metal electrode serving as a top electrode deposited and patterned on the piezoelectric layer; and ZnO-based nanostructures deposited and patterned on a top surface of the top electrode; wherein wettability (from super hydrophobicity to super hydrophilicity, or vice versa) of the ZnO-based nanostructures can be controlled; and a real-time signal analyzing device connected to the sensor device.

In one embodiment, the sensor device is a quartz crystal microbalance (QCM). In another embodiment, the sensor device is a thin-film bulk acoustic resonator (TFBAR).

In yet another embodiment, the ZnO-based nanostructures include undoped or doped ZnO or ternary $Mg_xZn_{1-x}O$. In one embodiment, the surface morphology of the ZnO-based nanostructures is selected from substantially flat, rough, and sharply uneven and achieved during the growth of the nanostructures. In another embodiment, the hydrophilicity of the ZnO-based nanostructures reduces the sensor's liquid sample consumption and enhances the sensitivity significantly.

In one embodiment, the monitoring system is capable of dual mode operation: producing acoustic and optical signals simultaneously or separately for analysis. In another embodiment, the optical signal is fluorescent light emitted from living cells growing on the surface of the ZnO-based nanostructures. In yet another embodiment, the acoustic signal is acoustic admittance in the BAW sensor device.

Also provided is a method for monitoring dynamic behavior of cell adhesion and proliferation using the monitoring system of the present invention, wherein the method includes generating time-frequency signals with the monitoring system and extracting spectral shape evolution data, peak frequency shift data, motional resistance data, and motional induction data from the time-frequency signals using a data simulation and modeling technique based upon a Butterworth-Van-Dyke (BVD) lumped-parameter model.

BRIEF DESCRIPTION OF THE DRAWINGS

FIG. 4 shows time-evolving frequency shift (deviation from resonance frequency) for the standard QCM (solid squares), and the $ZnO_{nano}$-QCM (open circles) showing ~10 times enhanced sensing performance by the $ZnO_{nano}$-QCM.

FIG. 5 (a) shows the mechanical impedance model of the $ZnO_{nano}$-QCM cell monitoring system and (b) provides the corresponding electrical circuit model of the $ZnO_{nano}$-QCM cell monitoring system.

FIG. 7 shows (a) a time-evolving $S_{21}$ spectra of a standard QCM showing very little changes to amplitude modulation during the 60-hour cell monitoring cycle, (b) 20× fluorescence image of BAEC cells in full confluency on the sensing area of the standard QCM; (c) time-evolving $S_{21}$ spectra of an embodiment ZnO nano-QCM with rough ZnO columns which show both amplitude modulation and (e) upward frequency-shifting which indicates variation in stiffness of the cells due to adhesion and proliferation. The cells also reached full confluency on the ZnO nano-QCM as shown on the 20× fluorescence image of its sensing area (d).

FIGS. 8(a) and (b) provide time-evolving Nyquist plots of the standard QCM showing very little changes to amplitude modulation during the 60-hour cell monitoring cycle. (c) and (d) provide time-evolving Nyquist plots of an embodiment of ZnO nano-QCM with rough ZnO columns which show both motional inductance and motional resistance. The rotation of the Nyquist plot over time indicates the instability of the acoustic resonance due to cell activity (proliferation and adhesion). After 35 hours the rotation stops indicating full confluency. The radius of the Nyquist plots have an inverse relation to the stiffness of the cells.

FIG. 9 (a) shows the time-evolving load resistance of the ZnOnano-QCM due to the adhering and proliferating cells, (b) illustrates the time-evolving load inductance of the ZnO nano-QCM. (c) and (d) show the motional resistance and inductance respectively of the standard QCM. (e) shows the load resistance versus reactive load plot of the $ZnO_{nano}$-QCM showing an upward curvature.

DETAILED DESCRIPTION OF THE INVENTION

Figure 1:
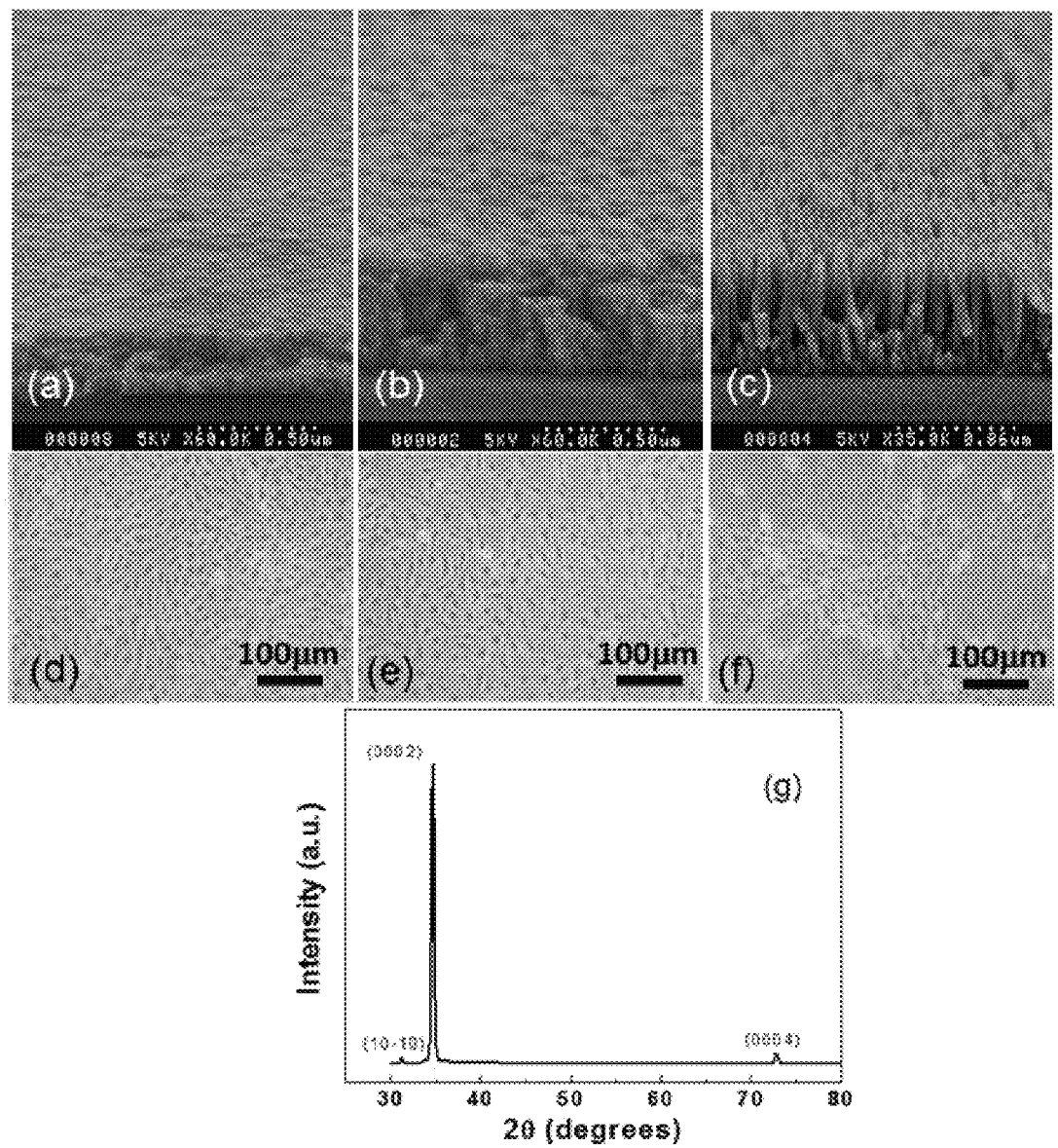
FIG. 1 includes FESEM images of the different surface morphologies of ZnO nanostrcutures grown on glass substrates: (a) flat columns, (b) rough columns (c) nanotips. These surfaces were treated with fibronectin and seeded with BAEC cells. Transmission type optical microscope images of the growing BAEC cells on (d) flat ZnO columns, (e) rough ZnO columns, and (f) sharp ZnO nanotips. (g) XRD plot of the ZnO nanotips grown on glass showing single crystalline structure with c-axis orientation.

A biosensor is a device which is capable of providing analysis of various analytes or biomolecules using biological recognition elements which are combined with a signal transducer. Generally, the sensor will produce a signal that is quantitatively related to the concentration of the analytes, or the transitions of biophysical states of the biological samples being sensed.

The biological recognition elements serve to recognize the analytes. These elements include enzymes, microorganisms, tissues, antibodies, receptors, nucleic acids, organelles or whole cells.

Transducers are physical components of the biosensor that respond to the products of the biosensing process and outputs the response in a form that can be amplified, stored or displayed. Biosensing occurs only when the analyte is recognized specifically by the biological element. Biological recognition in vivo at a single cell level is characterized by high sensitivity, fast response, specificity and reversibility.

A "sensor surface" refers to the location upon which a binding partner is immobilized for the purpose of measuring changes in physical properties, such as optical refractive index, electrical conductivity, mass loading, etc. They include, but are not limited to, semiconductor, metal and dielectric surfaces.

ZnO is emerging as a wide bandgap semiconductor. ZnO is particularly attractive as a sensor material due to its multifunctional properties. ZnO can be grown with various morphologies such as thin films and nanostructures on a large number of substrates including insulators such as glass, quartz, $Al_2O_3$; semiconductors such as Si, GaAs, GaN, and SiC; electrodes such as metals and transparent conductive oxide (TCO); and also on the flexible substrates such as polymers. As used herein with respect to surface morphology of the nanostructures, the phrase "substantially flat" is defined as a substantially even surface. "Rough" is defined as a surface marked by irregularities, protuberances, and/or ridges. "Sharply uneven" is defined as an uneven surface containing sharp points (e.g. nanotips).

The ZnO-based nanostructures of the present invention are made from undoped or doped ZnO or its ternary alloy, such as magnesium zinc oxide ($Mg_xZn_{1-x}O$) which can be grown on a substrate by metal-organic chemical vapor deposition (MOCVD) and other deposition technologies, then patterned by photolithography and etching process. Undoped ZnO and its nanostructures show n-type semiconducting behaviors. Dopants are introduced to modify the physical properties of the ZnO-based nanostructures and make it multifunctional to benefit various sensing applications. For example, group III-donors like Al and Ga significantly enhance electrical conductivity; transitional metal (TM) dopants like Fe and Mn make it ferromagnetic; compensational dopants like Cu and Ni make it piezoelectric.

A dynamic and noninvasive method of monitoring the adhesion and proliferation of biological cells, for example, the bovine aortic endothelial cells (BAEC) using a ZnO-based nanostructure biosensor is disclosed. In one embodiment, the monitoring system includes a $CO_2$ incubator; a temperature control device deployed inside the incubator; one or more cell-growth wells deployed inside the incubator; a bulk acoustic wave (BAW) sensor device deployed inside at least one cell-growth well wherein the sensor device includes: a piezoelectric layer; a conductive film serving as a bottom electrode deposited and patterned beneath the piezoelectric layer; a metal electrode serving as a top electrode deposited and patterned on the piezoelectric layer; and ZnO-based nanostructures deposited and patterned on a top surface of the top electrode; wherein wettability (from hydrophobicity to hydrophilicity, or vice versa) of the ZnO-based nanostructures can be controlled; and a real-time signal analyzing device connected to said sensor device. Wettability states can also range from super hydrophobicity to super hydrophilicity, Especially for the ZnO nanostructures with tip-type of sharp surface morphology. The hydrophilicity of the ZnO-based nanostructures can reduce the sensor's liquid sample consumption and enhance the sensitivity significantly.

The BAW sensor device deployed into the cell monitoring system can be a ZnO nanostructure-modified QCM or TFBAR.

The piezoelectric material used in the BAW can be, but is not limited to, quartz, $LiNbO_3$, $LiTaO_3$, ZnO and the like. The metal electrodes are deposited and patterned using the standard microelectronic processing techniques.

The ZnO-based nanostructure moidifed BAW ($ZnO_{nano}$-BAW) sensor operates similarly to a BAW resonator device. The BAW resonator will resonate at a specific frequency determined by the piezoelectric substrate material properties and thickness. When bonding of the target occurs on the ZnO-based nanostructures, mass-loading results with a shift in the resonance frequency of the resonator, directly proportional to the amount of target material bonded to the ZnO-based nanostructures.

The ZnO nanostructure modified-QCM ($ZnO_{nano}$-QCM) biosensor can include a conventional QCM with ZnO-based nanostructures directly grown on its sensing electrode. Methods employ the ($ZnO_{nano}$-QCM) biosensors deployed in-situ of a standard cell culture environment. The nano-QCM biosensor displays enhanced sensitivity in real-time over the standard QCM as it not only detects the mass accumulation but also the viscoelastic transitions relating to biophysical cell activity such as adhesion and proliferation. The time-evolving acoustic spectra, real-time frequency shifts, as well as the dynamic Nyquist plots and dynamic motional impedances of the ($znO_{nano}$-QCM) reveal viscoelastic transformations during the early seeding and adhesion stage in the cell growth. Cellular confluency or the maximum proliferation is detected when the temporal components of the acoustic spectra, motional resistance and inductance, and the Nyquist plots reach the steady state. The confluency of the cells growing on the nano-QCM is verified by fluorescence imaging by replacing the regular cell medium with a fluorescent-tagged medium.

In another embodiment of the present invention, the ZnO-based nanostructures can be incorporated into a thin film bulk acoustic resonator ($ZnO_{nano}$-TFBAR). The TFBAR can operate at much higher frequencies. TFBAR consists of a piezoelectric film sandwiched by a top and bottom electrodes. It has many advantages, such as small size, low insertion loss and lower power consumption. In addition, TFBAR sensors are much smaller, and can be readily integrated as arrays. The TFBAR sensors can be integrated with other Si-based electronic components on the same substrate and compatible with small-size microwave aerials, and hence can be used for wireless distance probing.

By controlling the morphology of the ZnO-based nanostructure surfaces (thin film or substantially flat, rough surface, and nanotips), it can attach to certain biological cell lines (i.e., NIH 3T3 fibroblasts, umbilical vein endothelial cells, and capillary endothelial cells.) and control the extent of cellular adhesion. ZnO-based nanostructures can also be used to bind with bacterial and viral cultures for reaction with enzymes and antibodies for applications in immunosensing.

The current invention of $ZnO_{nano}$-QCM takes advantage of the unique sensing ability and biocompatibility of ZnO-based nanostructures and combine them with the QCM method of dynamic noninvasive and label-free cell monitoring. Furthermore, it combines the multifunctional properties of ZnO films and nanostructures as both the biomolecular interface and the sensitivity-enhancing material to form the $ZnO_{nano}$-QCM cell monitoring sensor. This greatly enhances the sensitivity of the measurements, allows for simultaneous multiple parameters output in a single measurement, enables noninvasive testing, and allows for portable and cost effective design. The biophysical properties, mainly viscoelastic transitions, mass accumulation, and cell monolayer adhesion and proliferation relating to cell activity can be monitored in real-time through the specific time-evolving sensor spectral signatures (i.e., spectral shape, Nyquist characteristics, and peak frequency shifting).

Also presented is a method for monitoring dynamic behavior of cell adhesion and proliferation by generating time-frequency signals with the monitoring system of the present invention and extracting spectral shape evolution data, peak frequency shift data, motional resistance data, and motional induction data from the time-frequency signals using a data simulation and modeling technique based upon a Butterworth-Van-Dyke (BVD) lumped-parameter model.

Material Preparation and Experimental Procedures

A. ZnO Growth with Various Surface Morphologies

ZnO films of various surface morphologies were grown on 22 mm square glass cover slips (Fisher Scientific, Pittsburgh, Pa.) by the metal-organic chemical vapor deposition (MOCVD) technique to serve as the test substrates to determine the optimal ZnO surface for cellular adhesion. Diethylzinc (DEZn) and ultra-high purity (UHP>99.999%) $O_2$ are used as the Zn precursor source and oxidizer, respectively. A chamber pressure of ~50 Torr was maintained during the growth. For achieving various surface morphologies of ZnO films, we adjusted the substrate temperature and simultaneously the growth rate by tuning the $DEZn/O_2$ flow rate ratio, which are ~500° C. and 65/1500 ($DEZn/O_2$ flow rate ratio) for the sharply uneven structures (e.g. nanotips), ~430° C. and 100/1500 for the nano-columns with flat ends (e.g. substantially flat structures) and ~330° C. and 100/1500 for the nano-columns rough ends (e.g. rough structures). The film thickness was well-controlled by adjusting the growth time under a fixed growth rate. FIG. 1($a$-$c$) shows the three different ZnO morphologies used for the adhesion control experiment. FIG. 1($a$) shows the densely packed nano-columns of ~300 nm height, ~10 nm width, and flat ends. The aggregate collection of these columns forms a relatively flat top surface (in this paper we shall refer to this as the "substantially flat" surface morphology). We obtained a field emission scanning electron microscope (FESEM) to image the different morphologies of our grown ZnO nanostructures. FIG. 1(b) shows the densely packed nano-columns with ~500 nm height and ~10 nm width with jagged tips which collectively form a rough top surface (in this paper we shall refer to this as the "rough" surface morphology). FIG. 1(c) shows well-ordered nano-rods with ~600 nm height and <10 nm width and sharp tips which collectively form a sharp surface (in this paper we shall refer to this as the "sharply uneven" surface morphology). The surface roughness (root mean square) of these ZnO films was characterized by AFM, which is 1.39 nm for the "flat" ZnO, 7.48 nm for the "rough" ZnO, and 11.4 nm for the "sharp" ZnO samples. The crystallographic orientation and structural quality of the as-grown ZnO films on glass are determined using a Bruker D8 Discover four-circle x-ray diffractometer (XRD). FIG. 1(g) shows an x-ray $\theta$-$2\theta$ scan of ZnO nanotips grown on glass. The scan is done using CuK$\alpha$ radiation to analyze the orientation of the ZnO films. The ZnO (0002) peak at $2\theta$ about 34.7° is observed, indicating a predominantly c-axis oriented ZnO (0002) nanostructures on the glass substrate. This peak confirms the wurtzite structure of the grown ZnO. After material characterization, each sample was sterilized with ethyl alcohol and distilled water and then treated with the human fibronectin (BD Biosciences, Bedford, Mass.) and placed in a standard 6-cell well and filled with cell medium for standard cell growth analysis.

B. Preparation of the $ZnO_{nano}$-QCM Cell Monitoring Sensor

Figure 2:
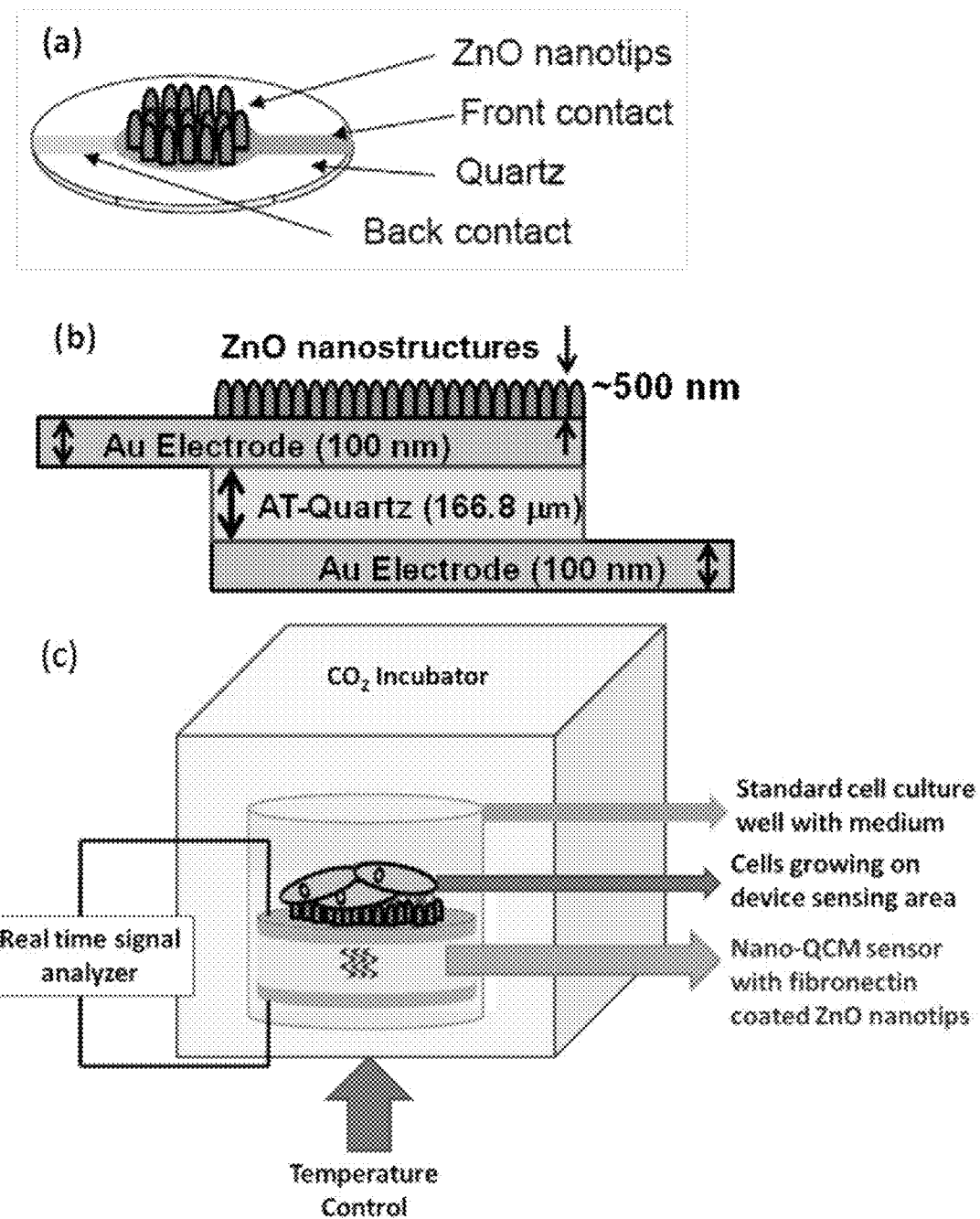
FIG. 2 provides (a) A ZnO nanostructure-based nano-QCM biosensor schematic, (b) its multilayer (c) time-evolving acoustic spectrum of the ZnO nano-QCM shows both amplitude reduction (c) setup for deploying the ZnO nano-QC biosensor for noninvasive and dynamic cell growth monitoring.

The $ZnO_{nano}$-QCM device comprises ZnO nanostructured arrays that are integrated on a standard low cost AT-cut QCM by growing the nanostructures directly on the sensing area of the QCM using MOCVD through a shadow mask. The optimal ZnO nanostructure morphology was determined through the control of the MOCVD growth conditions described above. The $ZnO_{nano}$-QCM device schematic is shown in FIG. 2(a) and its multilayer structure in FIG. 2(b). The piezoelectric AT-cut quartz layer is sandwiched between two 100 nm gold electrodes. The quartz substrates have a diameter of 1.37 cm and the sensing area is 0.2047 cm$^2$. ZnO nanostructure layer has ~500 nm. The ZnO-covered sensing area was exposed to UV light for 10 minutes to make it superhydrophilic. The combined effect of very high effective surface area of the nanostructures and superhydrophilic state will make the $ZnO_{nano}$-QCM a very sensitive mass measuring device as well as a monitoring device for viscoelastic transitions in the sample. Moreover, the use of the ternary alloy magnesium zinc oxide ($Mg_xZn_{1-x}O$) nanostructures instead of pure ZnO nanostructures adds the ability of the sensor to extend its pH sensitivity range. This expands the types of biological cell species that can be analyzed by out claimed device.

The $ZnO_{nano}$-QCM was then deployed inside a Teflon cell-growth well to serve as the test device (FIG. 2(c)), while a standard QCM was inserted in a similar Teflon cell-growth well to serve as the control device. The control and test devices were both sterilized with ethanol and de-ionized water and then surface-treated with human fibronectin for 1.5 hours. The Teflon well was filled with growth medium, and seeded with bovine aortic endothelial cells (BAEC). They were then placed in a standard $CO_2$ incubator for 60 hours. The acoustic admittance spectra of the deployed devices were measured in real-time for 60 hours while the cells were actively growing on each device.

C. Cell Culture Protocol

The cell line used for all experiments was bovine aortic epithelial cells (BAEC). All cells were maintained in the standard humidified incubator (5% $CO_2$ and 95% air) at 37° C. The cells were grown in low glucose Dubelcco's modified eagle medium (DMEM) supplemented with 1% L-Glutamine, 1% bovine brain extract (BBE) (Clonetics, Inc.), 0.5% Heparin, 10% fetal bovine serum (FBS), and 0.4% of 10,000 U/ml penicillin and 10,000 mg/ml streptomycin solution. The cell culture was trypsinized and diluted for re-seeding after ~85% confluency was reached.

After full confluency standard optical microscopy was used to monitor the cells grown on the ZnO-on-glass samples that were placed inside the 6-well cell culture plates. Since the $ZnO_{nano}$-QCM and standard QCM device are optically opaque, to confirm the growth of living cells on the $ZnO_{nano}$-QCM after the entire monitoring cycle, the growth medium was modified with a fluorescent living-cell tracer (Cell Tracker Orange CMRA) by preparing a 1:5 solution of CMRA fluorescent tracker and dimethyl sulfoxide (DMSO) to the growth medium. The fluorescent-tagged living cells growing on the active sensing area of the device were imaged using an Axiovert 200M confocal fluorescence microscope (Zeiss Axiovert 200M, Gottingen, Germany) with a 548 nm filter and 576 nm excitation to obtain reflection type fluorescence images.

D. $ZnO_{nano}$-QCM Measurement and Data Analysis

The characterization and testing of the $ZnO_{nano}$-QCM and standard QCM devices was conducted using an HP 8573D Network Analyzer (Agilent Technologies, Palo Alto, Calif.). The acoustic admittance (Y) spectrum of the device was automatically measured in every half-hour interval while the BAEC cells were growing on the $ZnO_{nano}$-QCM sensor inside the incubator. The final output of the $ZnO_{nano}$-QCM cell monitoring sensor will be in the form of time-frequency 3D signals that contain in itself multiple parameters in a single monitoring period namely (i) spectral shape evolution, (ii) peak frequency shift, (iii) Nyquist radius evolution and rotation, (iv) dynamic motional resistance and inductance. Each of these parameters was analyzed for correspondence to the dynamic behavior of cell adhesion and proliferation and will be discussed below.

Results and Discussion

A. Adhesion of BAEC Cells on ZnO Surfaces with Various Morphologies

It may be desirable to determine the most suitable ZnO nanostructure morphology to facilitate the optimal adhesion of the cells to the device. In order to determine the optimum morphology for the cell adhesion, ZnO nanostructures with three different surface morphologies were grown on glass substrates using MOCVD: flat, rough and sharp surfaces. The method of attaining these ZnO surfaces was discussed above. The FESEM images for the three types of morphologies are shown in FIG. 1(a-c). All ZnO samples range from 300-600 nm thickness, with single crystal quality and c-axis-preferred orientation (FIG. 1(g)). The surfaces of the three samples were then treated with fibronectin which serves as the biochemical layer that facilitates initial cell anchorage to ZnO. The surface treated samples were then placed in a standard 6-well cell culture plate containing growth medium for BAEC cell seeding. The samples were incubated for 48 hours in a standard $CO_2$ incubator. The standard transmission type optical microscope images of the three ZnO samples were taken after 48 hours of incubation. For the flat ZnO surface, the cell culture is close to 100% confluency and uniformly spreading and proliferating on the ZnO substrate (FIG. 1(d)). However, after the entire duration of the monitoring cycle the cells have already crowded with each other and competing for nutrients and space. This condition will eventually induce the cells to die and detach from the ZnO surface. On the other hand, the cells on the rough ZnO surface have reached about 75% confluency, uniform proliferation, and the individual cells have considerable amount of spreading as shown in FIG. 1(e). The cells adhered to the sharp ZnO surface, but the cells did not establish good focal adhesion to facilitate uniform proliferation nor proper individual cell spreading. The cell culture on the sharp ZnO surface only attained 40% confluency and a clumped cell distribution as shown in FIG. 1(f). This clumped distribution might cause localized areas on the ZnO surface where cell death is induced. To obtain a good cell culture for monitoring purposes, three components of cell growth are preferably satisfied (i) good initial cell adhesion, (ii) uniform cell proliferation, and (iii) considerably large individual cell spreading. The flat and rough ZnO surfaces displayed all three while the sharp ZnO surface failed to fulfill the last two requirements. It would be a natural choice to use the flat ZnO surface since it gives us a large yield in cell growth while fulfilling all three cell culture requirements. However, there is an inherent tradeoff in choosing the optimal ZnO morphology for the sensing surface. In terms of cell attachment, the cells favor the adhesion to flatter surfaces, but in terms of device performance the shaper surface provide the highest sensitivity due to the large effective sensing area provided by the nanostructures. It is determined that the rough ZnO surface may be the most suitable morphology for adhesion and viability for cell growth without sacrificing the device sensitivity.

Figure 3:
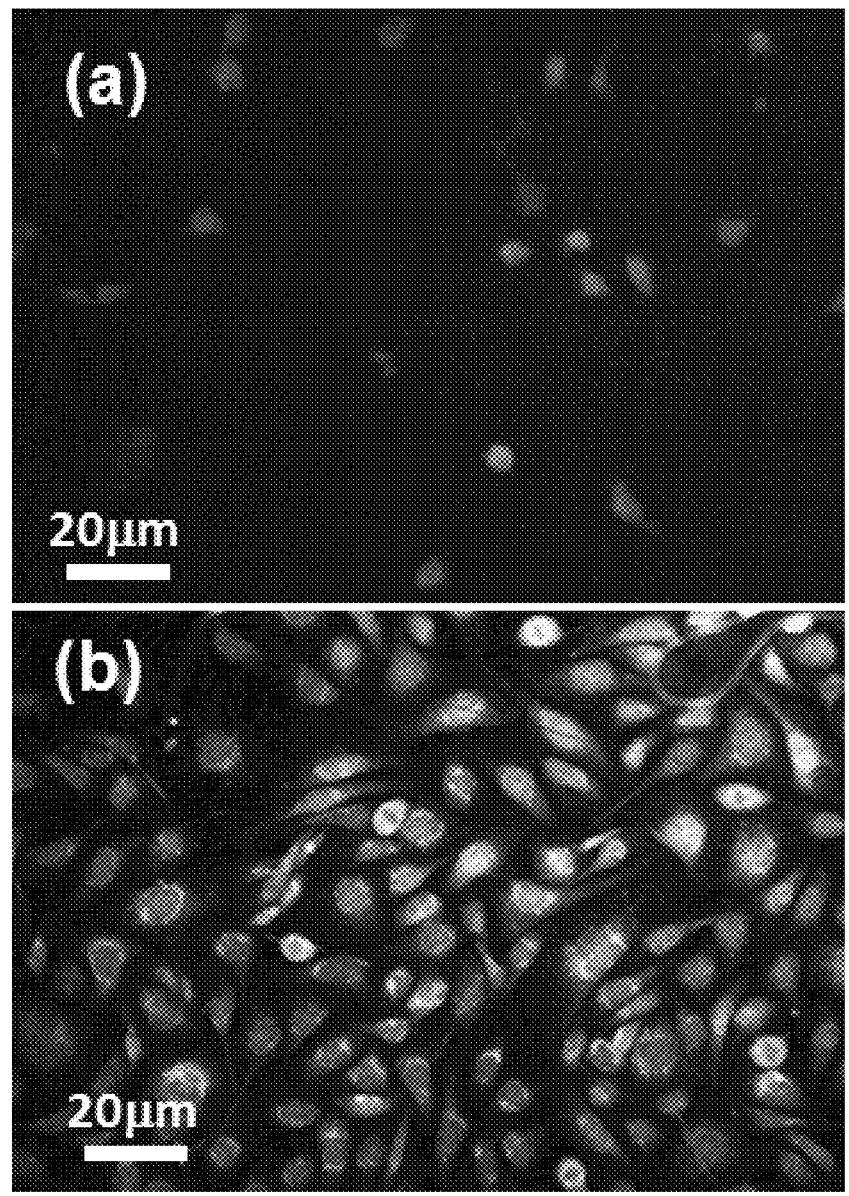
FIG. 3 provides fluorescence micrographs of BAEC cells growing on the nano-QCM sensing area with (a) sharp ZnO nanotips and (b) rough ZnO columns, after 48 hours of incubation, in which living cells were stained with Cell Tracker fluorescent tag.

For comparison, we repeated the same cell adhesion experiment on two different $ZnO_{nano}$-QCM devices; one with the rough ZnO surface and another with the sharp ZnO surface grown on the top electrode. Since the devices are opaque due to the electrodes, standard transmission type optical microscopy is not possible for imaging the cells growing on the device. To achieve the imaging of the cells, we modified the growth medium by introducing CMRA fluorescent tracker to allow for fluorescence imaging of the living cells growing on the nano-QCM surface. FIGS. 3(a) and (b) show the fluorescence images of the living cells on the $ZnO_{nano}$-QCM with sharp and rough surface, respectively. The fluorescence micrograph representing the nano-QCM with sharp surface shows low cell attachment and proliferation whereas the one of the rough surface shows uniform cell proliferation, good attachment and individual cell spreading.

C. Cell Monitoring Using $ZnO_{nano}$-QCM

The $ZnO_{nano}$-QCM device with the optimized ZnO surface morphology (rough ZnO surface) was utilized to monitor adhesion and proliferation of the cells. A standard QCM was deployed inside a Teflon cell-growth well to serve as a control device while a $ZnO_{nano}$-QCM was inserted in a similar Teflon cell-growth well to serve as the test device. The control and test devices were both surface treated with fibronectin, filled with growth medium and stand for an hour in the incubator to let the devices reach stability, and the medium to reach stable pH before the cells are seeded with BAEC cells. They were then placed back in the incubator for 60 hours. While the cells were growing on each device, we continuously measured the sensor's acoustic parameters for half-hour intervals.

The time-evolving resonance frequency shift $\delta f(t) = f_0 - f(t)$ were monitored for both the standard QCM and the ZnO nano-QCM, where $f_0$ is the resonant frequency of the device before cell seeding and $f(t)$ is the subsequent resonant frequency of the device after a time t. FIG. 4 and its inset show the plot of $\delta f(t)$ for both devices. The most evident feature of this plot is the enhanced sensitivity of the $ZnO_{nano}$-QCM over the standard QCM where the maximum frequency shift at confluence of the $ZnO_{nano}$-QCM is ~10 times larger than the standard QCM. This can be attributed to the giant effective surface area made available for cell attachment to the ZnO nanostructures on the sensing area of the $ZnO_{nano}$-QCM device. Adding the ZnO nanostructures to the QCM sensing area enhances this interfacial interaction by providing a huge effective sensing area for the device. The $ZnO_{nano}$-QCM device also exhibits a linear cell proliferation from initial seeding before it tapers off at 40 hours when the cells reach full confluency. The standard QCM on the other hand shows nonlinear proliferation rate (FIG. 4, plot with square symbols) and reaches confluency early at 25 hours of incubation.

The mechanical model corresponding to the claimed cell monitoring system is shown in FIG. 5(a). This mechanical model can be expressed in the electrical equivalent circuit model called the Butterworth-van-Dyck (BVD) equivalent circuit model of the cell monitoring system which is shown in FIG. 5(b) and is composed of a series RLC circuit in parallel with a capacitor $C_0$. The capacitor $C_0$ represents the total capacitance of the dielectric quartz sandwiched between two Au electrodes. This capacitance describes the basic characteristics of the resonator far from the resonance frequency. The branch of the circuit that represents the motional characteristics of the nano-QCM near and at the resonance frequency is the series RLC circuit, composed of $R_Q$, $L_Q$, and $C_Q$, the motional resistance, inductance and capacitance of the quartz resonator at no load, respectively. Since the ZnO layer is rigidly attached to the Au electrode and is thin enough relative to the Au electrode, we can lump together the effect of ZnO to the no-load parameters. When the $ZnO_{nano}$-QCM experiences mechanical perturbations due to a viscoelastic load placed on its sensing electrode, an additional series RL circuit ($R_{Load}$ and $L_{Load}$) should be included in series with the no-load parameters. This additional RL circuit represents the dynamic load on the $ZnO_{nano}$-QCM which comprises the electrical load impedance ($Z_{Load}$) due to the attached mechanical load on the sensing area of the device given by:

$$Z_{Load} = R_{Load} + j\omega_o L_{Load} \quad (1)$$

where $j = \sqrt{(-1)}$ and $\omega_o$ is the resonant frequency of the device. According to Brandey et al. the multilayer system comprising the QCM can be $Z_{Load}$ is directly related to the mechanical impedance experienced by the acoustic wave due to the physical perturbations occurring at the attached overlaying material given by the expression:

$$R_{Load} = \frac{1}{Y_{Load}} \frac{\pi}{4K^2(\omega_0 - \Delta\omega)C_0} \frac{Z_{mechLoad}}{Z_{mechQCM}} \quad (2)$$

where $K^2$ is the coupling coefficient of the piezoelectric quartz layer, $\Delta\omega$ is the frequency shift due to the rigid ZnO nanostructured layer, $Z_{mechLoad}$ and $Z_{mechQCM}$ are the mechanical impedances of the cellular layers attached to the sensing area, and the QCM respectively. Eq. (1) and (2) give the expression for $R_{Load}$ and $L_{Load}$ and are related to the measured admittance parameter by:

$$R_{Load} = \frac{\pi}{4K^2\omega_0 C_0} \frac{\text{Re}\{Z_{mechLoad}\}}{Z_{mechQCM}} = \frac{\text{Re}\{Y_{Load}\}}{\text{Re}^2\{Y_{Load}\} + \text{Im}^2\{Y_{Load}\}} \quad (3)$$

$$L_{Load} = \frac{\pi}{4K^2\omega_0 C_0} \frac{\text{Im}\{Z_{mechLoad}\}}{Z_{mechQCM}} = \frac{-\text{Im}\{Y_{Load}\}}{\omega_0(\text{Re}^2\{Y_{Load}\} + \text{Im}^2\{Y_{Load}\})} \quad (4)$$

The quantity $R_{Load}$ corresponds directly to the mechanical or motional resistance and designates dissipation of acoustic energy due to the attached cell growth layer on the $ZnO_{nano}$-QCM surface. The parameter $L_{Load}$ on the other hand is directly proportional to the stored energy by the cell layer (i.e. elasticity increase).

$Y_{Load}$ is the measured admittance spectrum minus the no-load admittance spectrum of the standard QCM. Adapting our cell monitoring setup to the $Z_{mechL}$ expression developed by (Bandey et. al., 1997), the mechanical impedance becomes a combination of the mechanical effects derived from the mechanical model in FIG. 5(a) and is given by Eq. (5)

$$Z_{MechL} = j\omega\rho_{ZnO} + Z_{cell}\left[\frac{Z_{Medium}\cosh(\gamma_{cell}h_{cell}) + Z_{cell}\sinh(\gamma_{cell}h_{cell})}{Z_{cell}\cosh(\gamma_{cell}h_{cell}) + Z_{Medium}\sinh(\gamma_{cell}h_{cell})}\right] \quad (5)$$

where $j\omega\rho_{ZnO}$ represents the impedance of the rigid ideal mass ZnO nanostructured layer, $Z_{cell}=\rho_{Cell}G_{Cell}$ is the impedance of the finite-thickness ($h_{cell}$) viscoelastic cell layer, and $z_{medium}$ is the impedance of the growth medium as a semi-infinite Newtonian fluid, which is given by $$Z_{Medium} = (1+j)\sqrt{(\omega\rho_{medium}\eta_{medium}/2)} \quad (6)$$

Figure 6:
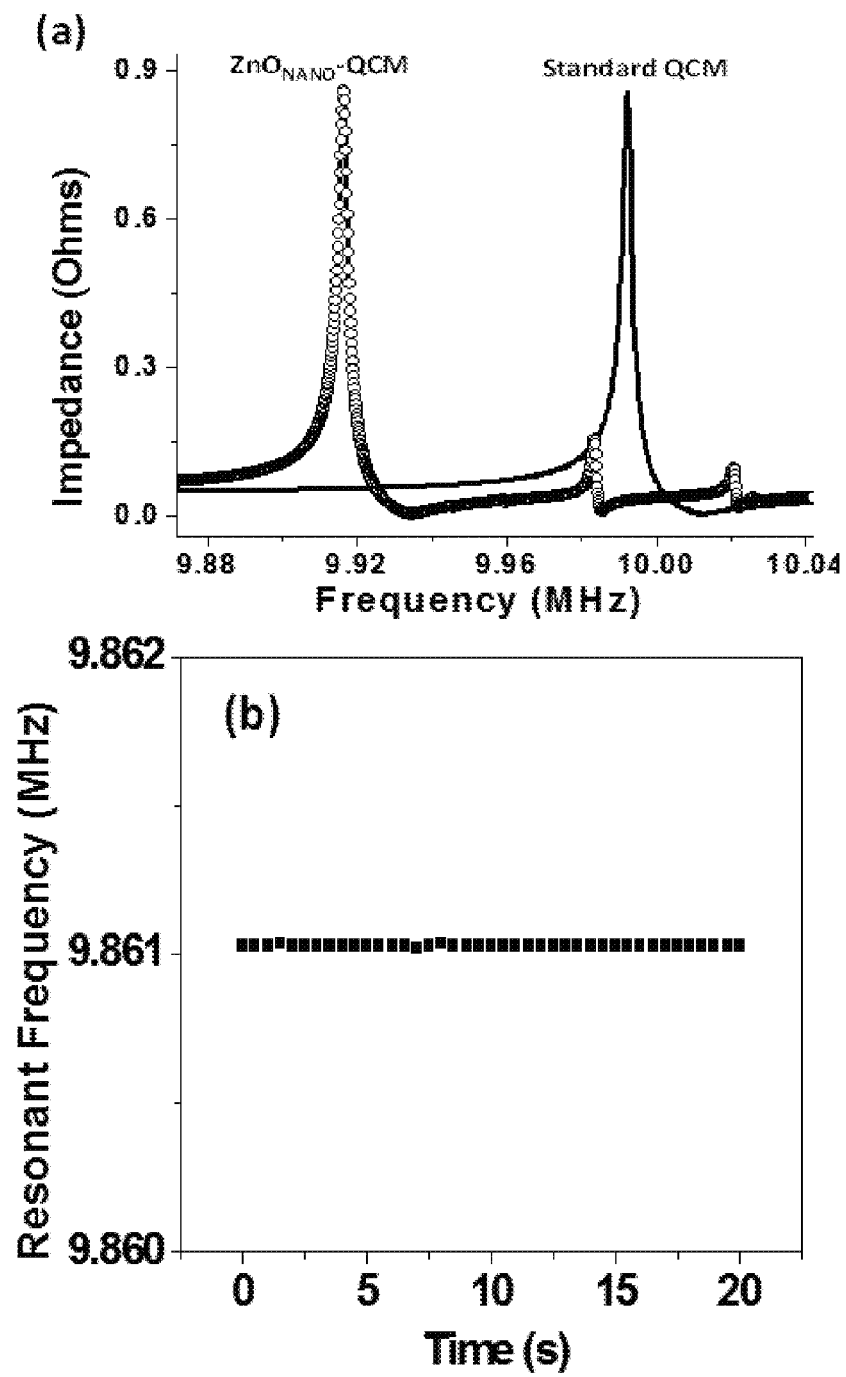
FIG. 6 shows (a) the impedance spectrum of the standard QCM (solid line), the $ZnO_{nano}$-QCM (open circles) (after ZnO nanostructure deposition) and (b) the time-evolving resonant frequency of the same $ZnO_{nano}$-QCM with the fibronectin and growth medium monitored for 20 hours.

To isolate the effects of the ZnO layer and the growth medium (and also obtain empirical values for the BVD parameters for these layers) we measured the admittance parameter of the $ZnO_{nano}$-QCM right after the ZnO nanostructure deposition on the sensing electrode to show that the only effect the ZnO film, the growth medium and fibronectin layers collectively does on the signal is to introduce a Sauerbrey frequency shift (FIGS. 6(a) and (b)) This means that the this collective layer does not contribute to the dynamic transitions occurring in the cell monitoring setup. These will serve as the baseline signals which verify that the changes we observed in the time-evolving admittance spectra are only due to the viscoelastic cell layer.

We used the time-evolving admittance parameter spectrum to analyze (i) spectral shape evolution, and (ii) direction of peak frequency shift. The time-evolving Nyquist plot is derived from the acoustic admittance by plotting Im{$Y_{Load}(\omega)$} versus Re{$Y_{Load}(\omega)$}, where Re{$Y_{Load}(\omega)$} and Im{$Y_{Load}(\omega)$} are the real and complex part of YLoad($\omega$), respectively. The Nyquist plot yields (i) the Nyquist radius evolution, and (ii) Nyquist rotation. The parameters extracted from $Y_{Load}(\omega)$ will provide dynamic information corresponding to viscoelastic transitions due to proliferation, adhesion and growth of the cells on the $ZnO_{nano}$-QCM biosensor.

FIG. 7 shows the time evolution of the acoustic transmission spectra of both devices. Shown in FIG. 7(a) is the time-evolving acoustic spectrum of the control device (standard QCM). The inset FIG. 7(b) shows the 20× fluorescence imaging of the cells reaching full confluency on the control device; however, its acoustic spectrum does not exhibit any changes. We applied the same growth conditions to the $ZnO_{nano}$-QCM, which exhibited more information than the control device. The time-evolving $Y_{Load}(\omega)$ spectrum of the $ZnO_{nano}$-QCM shows both periodic amplitude reduction and increase (FIG. 7(c)) and upward frequency-shifting (FIG. 7(e)) within the 60 hour incubation. The amplitude reduction indicates that the sample being monitored exhibits elastic properties and is dampening the acoustic waves resonating within the device. An increase in amplitude on the other hand indicates the sample's stiffening, making it act "solid-like" which contributes less to the acoustic wave dampening. An increase in the peak frequency also indicates the increase in stiffness of the samples. In FIG. 7(c) we see an initial increase in the amplitude of the $Y_{Load}(\omega)$ spectrum for the first 10 hours of the cell incubation then starts decreasing up to around 20 hours. This indicates that upon cell seeding the cells have not attached to the ZnO nanostructures yet but are just settled on the surface, resulting in a lower signal amplitude. However, as the cells start to adhere and proliferate on the nanostructures, the cells form a more solidly adhering layer that lessens the dampening of the acoustic waves in the sensor, causing the signal to increase amplitude. The signal amplitude reduction and increase happen again at 25 hours to 40 hours and then increase again and stay at that amplitude until the end of the monitoring cycle at 60 hours. The stabilized amplitude in the last 20 hours indicates that the cells have fully proliferated and reach full confluency on the entire sensing area. The cells have indeed reached full confluency on the $ZnO_{nano}$-QCM as shown on the 20× fluorescence image of the sensing area (FIG. 7(d)). It is difficult to explain the amplitude increase and reduction between 25 hours and 40 hours since the amplitude variation may or may not be due to the cell proliferation and adhesion alone since it might reflect viscoelastic transitions due to cell cycle transitions. The seeded cells have not been synchronized in growth during seeding so each individual cell will be transitioning in different cell growth phases while they are adhering and proliferating on the ZnO nanostructures. The current sensor system is not limited to only monitor the BAEC cell species, but also enables to monitor the adhesion and proliferation of other cell types.

Using time-evolving $Y_{Load}(\omega)$ data we performed a dynamic Nyquist analysis of both the standard QCM and the $ZnO_{nano}$-QCM. The Nyquist plot reveals additional information regarding the state of the cells growing on each device. The twisting of the Nyquist plot indicates the extent of viscoelastic stability within the range of the sensing area of the QCM, while the contraction and expansion of the Nyquist plot radius shows an inverse relationship to the cells' motional resistance on the sensing surface. See E. Nwankwo, C. J. Durning, "Fluid property investigation by impedance characterization of quartz crystal resonators Part I: Methodology, crystal screening, and Newtonian fluids," Sensors and Actuators, A72, 99-109, 1999. E. Nwankwo, C. J. Durning, "Fluid property investigation by impedance characterization of quartz crystal resonators Part II: Parasitic effects, viscoelastic fluids," Sensors and Actuators, 72, 195-202, 1999. Notice that for the standard QCM the time-evolving Nyquist plot does not show any indication of viscoelastic transitions during cell growth (FIG. 8(a-b)) for the entire 60-hour cell incubation period; on the other hand, the ZnO nano-QCM exhibits Nyquist twisting (FIG. 8(c)), and radius reduction and contraction (FIG. 8(d)) under the same cell growth conditions. In FIG. 8(c) we see that for the first 28 hours of cell culture, the Nyquist plot twists but stabilizes after 28 hours, indicating that the cells have reached uniform growth all over the sensing area (full confluency). In FIGS. 8(c) and (d), we also observe the periodic expansion and reduction of the Nyquist radius, indicating the growing cells' surface adhesion and transitioning viscoelasticity.

We used Eq. (3-4) to generate the motional resistance and inductance plots that relate the measured admittance spectra to the viscoelastic changes happening during the cell growth process monitored by the nano-QCM. FIG. 9(a) shows the motional resistance of the nano-QCM for the 40-hour cell growth monitoring period. The inset shows the same parameter for the standard QCM. The most obvious information derived here is the highly enhanced sensitivity of the nano-QCM compared to a standard QCM in detecting viscoelastic transition. For the standard QCM, the total change in motional resistance $\Delta R_{total}$ was only 1.5 k$\Omega$, while for the $ZnO_{nano}$-QCM it was 37.5 k$\Omega$ which is times higher than the standard QCM. FIG. 9(b) shows the motional inductance experienced by the $ZnO_{nano}$-QCM due to the cell growth. FIGS. 9(a) and (b) reveal certain details about the cell growth on the $ZnO_{nano}$-QCM sensor. $L_{Load}$ increases continuously from 0 to 40 hours while $R_{Load}$ changes in different time intervals. From 0 to 16 hours $R_{Load}$ increases slowly from 1.29 k$\Omega$ to 3.84 k$\Omega$. This indicates a small energy dissipation due to the low value of $R_{Load}$. This may be due to the onset of proliferation on the sensing area. For the time interval 16-30 hours there is a rapid increase in the value of $R_{Load}$ indicating a high energy dissipation that may be caused by the formation of more rigid focal adhesion points by the individual cells, and the increase of cell spreading. At 30-40 hours the value of $R_{Load}$ further increases faster indicating further energy dissipation due to onset of full confluency or cell crowding. This increase in energy dissipation is caused by the dampening of the shear waves induced by the large amount of cellular proliferation. FIGS. 9(c) and (d) show the motional resistance and inductance of the standard QCM respectively. FIG. 9(c-d) indicate that the total change in motional resistance and inductance of the standard QCM is significantly smaller than the total changes experienced by the $ZnO_{nano}$-QCM. This confirms the significant increase in sensitivity of the $ZnO_{nano}$-QCM compared to the standard QCM. FIG. 9(e) shows a plot of the motional resistance versus motional reactance. The upward curvature $$\frac{\partial^2 R_{Load}}{\partial (\omega L_{Load})^2} > 0$$

indicates that the energy loss per unit mass of the cells increases with the cell culture proliferation. The solid lines in FIGS. 9(a) and (b) represent the BVD fitting curves derived from empirical parameter fitting of the individual layers in the BVD model. The BVD model curves agree with the measured parameters; however, they do not closely fit because we did not include the energy lost to the transverse component of the acoustic waves that could be introduced by the ZnO nanostructures. The assumption in the model is that the cells have a constant density and have a uniform distribution on the entire sensing area. This model therefore approaches higher accuracy as confluency is reached rather than in the early proliferation stage.

The results demonstrate that the integration of ZnO nanostructures to the standard QCM device significantly increases the sensitivity of the biosensor, and provides a basis for performing noninvasive, real-time and dynamic label-free cellular monitoring.

The integration of ZnO nanostructures and a standard QCM forms a $ZnO_{nano}$-QCM, which possesses significantly enhanced sensitivity over the conventional QCM counterpart. The $ZnO_{nano}$-QCM is installed in situ using a standard cell culture environment for noninvasive and dynamic cellular monitoring. We have demonstrated the controlled adhesion and proliferation of BAEC cells on the nanostructured ZnO surface with the optimized surface morphology. The $ZnO_{nano}$-QCM exhibited enhanced sensitivity to detection of cell adhesion, proliferation, and viscoelastic transitions through a single measurement of time-frequency 3D acoustic spectra. The $ZnO_{nano}$-QCM shows 10 times increased sensitivity in frequency shift due to total cell proliferation in comparison with the standard QCM. The Butterworth-Van-Dyke (BVD) lumped-parameter model analysis was applied to the measured acoustic spectra to extract dynamic information from the signal's spectral shape evolution, peak frequency shift, and amplitude modulation. The presented technology provides a base for noninvasive, real-time, dynamic and label-free cellular monitoring.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A dynamic and noninvasive cell adhesion and cell proliferation monitoring system, comprising:
    a $CO_2$ incubator;
    a temperature control device disposed inside the incubator;
    one or more cell-growth wells deployed inside the incubator;
    a bulk acoustic wave (BAW) sensor device deployed inside at least one cell-growth well wherein the sensor device comprises:
        a piezoelectric layer;
        a conductive film serving as a bottom electrode deposited and patterned beneath said piezoelectric layer;
        a metal electrode serving as a top electrode deposited and patterned on said piezoelectric layer; and
        ZnO-based nanostructures deposited and patterned on a top surface of said top electrode; wherein wettability (from super hydrophobicity to super hydrophilicity, or vice versa) of said ZnO-based nanostructures can be controlled;
    and
    a real-time signal analyzing device connected to said sensor device.

2. The monitoring system of claim 1, wherein the sensor device is a quartz crystal microbalance (QCM).

3. The monitoring system of claim 1, wherein the sensor device is a thin-film bulk acoustic resonator (TFBAR).

4. The monitoring system of claim 1, wherein the ZnO-based nanostructures comprise undoped ZnO or ternary $Mg_xZn_{1-x}O$.

5. The monitoring system of claim 1, wherein the ZnO-based nanostructures comprise doped ZnO or ternary $Mg_xZn_{1-x}O$.

6. The monitoring system of claim 1, wherein the surface morphology of the ZnO-based nanostructures is selected from the group consisting of substantially flat, rough, and sharply uneven, and achieved during the growth of said nanostructures.

7. The monitoring system of claim 1, wherein the hydrophilicity of the ZnO-based nanostructures reduces the sensor's liquid sample consumption and enhances the sensitivity significantly.

8. The monitoring system of claim 1, wherein the system is capable of dual mode operation: producing acoustic and optical signals simultaneously or separately for analysis.

9. The monitoring system of claim 8, wherein the optical signal is fluorescent light emitted from living cells growing on the surface of the ZnO-based nanostructures.

10. The monitoring system of claim 8, wherein the acoustic signal is acoustic admittance in the BAW sensor device.

11. A method for monitoring dynamic behavior of cell adhesion and proliferation using the system in claim 1 comprising the steps of:

(a) generating time-frequency signals with the monitoring system of claim 1 and (b) extracting spectral shape evolution data, peak frequency shift data, motional resistance data, and motional induction data from the time-frequency signals using a data simulation and modeling technique based upon a Butterworth-Van-Dyke (BVD) lumped-parameter model.

* * * * *